US010588692B2

(12) United States Patent
Saba et al.

(10) Patent No.: US 10,588,692 B2
(45) Date of Patent: Mar. 17, 2020

(54) PULMONARY VEIN ISOLATION GAP FINDER

(71) Applicant: BIOSENSE WEBSTER (ISRAEL) LTD., Yokneam (IL)

(72) Inventors: Eitan Moshe Saba, Haifa (IL); David Izraeli, Haifa (IL); Meir Bar-Tal, Haifa (IL); Doron Moshe Ludwin, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 612 days.

(21) Appl. No.: 15/268,714

(22) Filed: Sep. 19, 2016

(65) Prior Publication Data

US 2017/0128128 A1 May 11, 2017

Related U.S. Application Data

(60) Provisional application No. 62/252,109, filed on Nov. 6, 2015.

(51) Int. Cl.
*A61B 34/10* (2016.01)
*A61B 18/14* (2006.01)
(Continued)

(52) U.S. Cl.
CPC ...... *A61B 18/1492* (2013.01); *A61B 18/1206* (2013.01); *A61B 34/10* (2016.02); *A61B 34/20* (2016.02); *A61B 90/37* (2016.02); *A61B 2017/00053* (2013.01); *A61B 2018/00375* (2013.01); *A61B 2018/00577* (2013.01); *A61B 2018/00791* (2013.01);
(Continued)

(58) Field of Classification Search
CPC . A61B 18/1492; A61B 18/1206; A61B 34/10; A61B 34/20; A61B 2034/105; A61B 2034/107; A61B 2034/2051; A61B 90/37; A61B 2090/374; A61B 2017/00053; A61B 2018/00375; A61B 2018/00577; A61B 2018/00791; A61B 2018/00839; A61B 2018/00875
See application file for complete search history.

(56) References Cited

U.S. PATENT DOCUMENTS 6,226,542 B1 5/2001 Reisfeld
6,301,496 B1 10/2001 Reisfeld
(Continued)

FOREIGN PATENT DOCUMENTS

EP   2 952 151 A1   12/2015
WO   WO 2011/145094 A2   11/2011
WO   WO 2012/092275 A1   7/2012

OTHER PUBLICATIONS

European Search Report dated May 18, 2017 from corresponding European Patent Application No. 16197331.8.

*Primary Examiner* — Thomas A Giuliani
*Assistant Examiner* — Catherine Premraj

(57) ABSTRACT

A gap between a plurality of ablation sites in a heart that hinders electrical propagation therethrough is found by projecting the locations of the sites in a 3-dimensional coordinate system onto a simulation plane, identifying a set of shortest 3-dimensional paths that correspond to 2-dimensional connections between pairs of the projected locations of the sites, and reporting a gap as a longest one of the set.

5 Claims, 17 Drawing Sheets

(51) Int. Cl.
  *A61B 34/20*    (2016.01)
  *A61B 18/12*    (2006.01)
  *A61B 90/00*    (2016.01)
  *A61B 17/00*    (2006.01)
  *A61B 18/00*    (2006.01)

(52) U.S. Cl.
  CPC ........... *A61B 2018/00839* (2013.01); *A61B 2018/00875* (2013.01); *A61B 2034/105* (2016.02); *A61B 2034/107* (2016.02); *A61B 2034/2051* (2016.02); *A61B 2090/374* (2016.02)

(56) References Cited

U.S. PATENT DOCUMENTS

| | | |
|---|---|---|
| 6,814,733 B2 | 11/2004 | Schwartz et al. |
| 6,892,091 B1 | 5/2005 | Ben-Haim et al. |
| 6,997,924 B2 | 2/2006 | Schwartz et al. |
| 7,156,816 B2 | 1/2007 | Schwartz et al. |
| 7,536,218 B2 | 5/2009 | Govari |
| 7,756,576 B2 | 7/2010 | Levin |
| 9,265,434 B2 | 2/2016 | Merschon et al. |
| 2011/0074779 A1* | 3/2011 | Voth ............... G06T 17/20 345/420 |
| 2014/0100563 A1 | 4/2014 | Govari et al. |
| 2014/0125653 A1 | 5/2014 | Massarwa |
| 2015/0018698 A1 | 1/2015 | Safran et al. |
| 2016/0095653 A1* | 4/2016 | Lambert ............ A61B 5/1076 606/41 |
| 2016/0247279 A1* | 8/2016 | Lavi ............... G16H 50/50 |

* cited by examiner

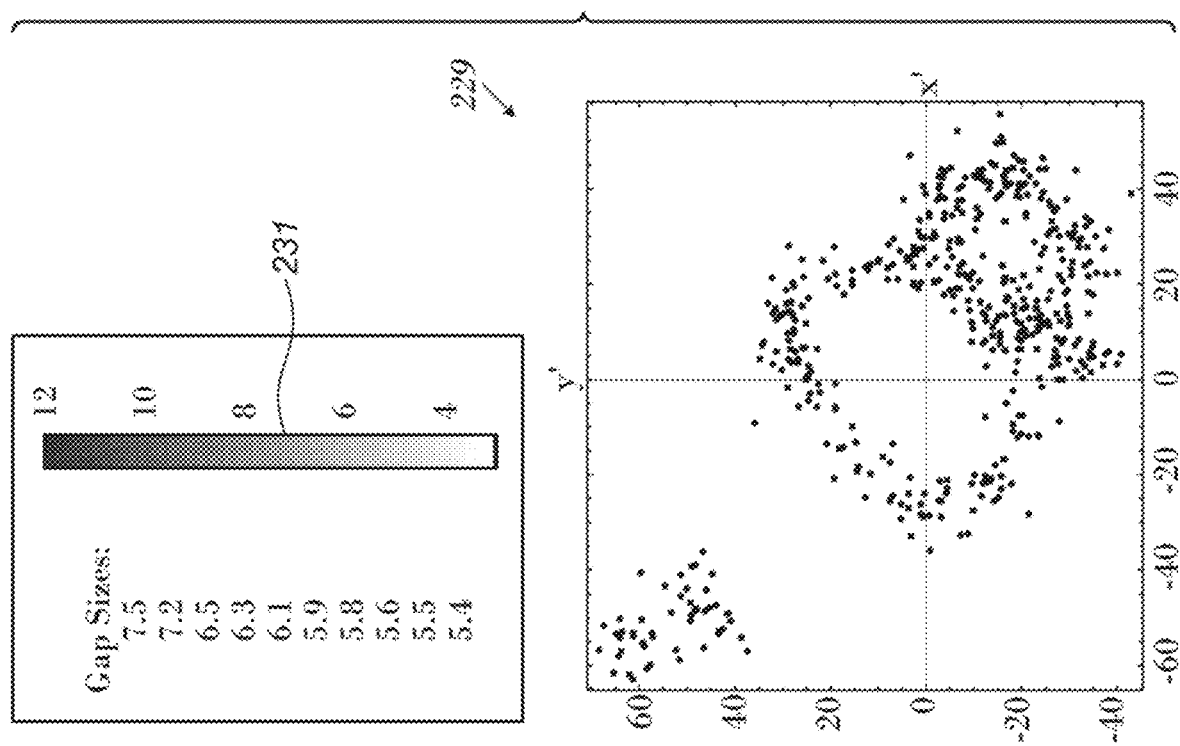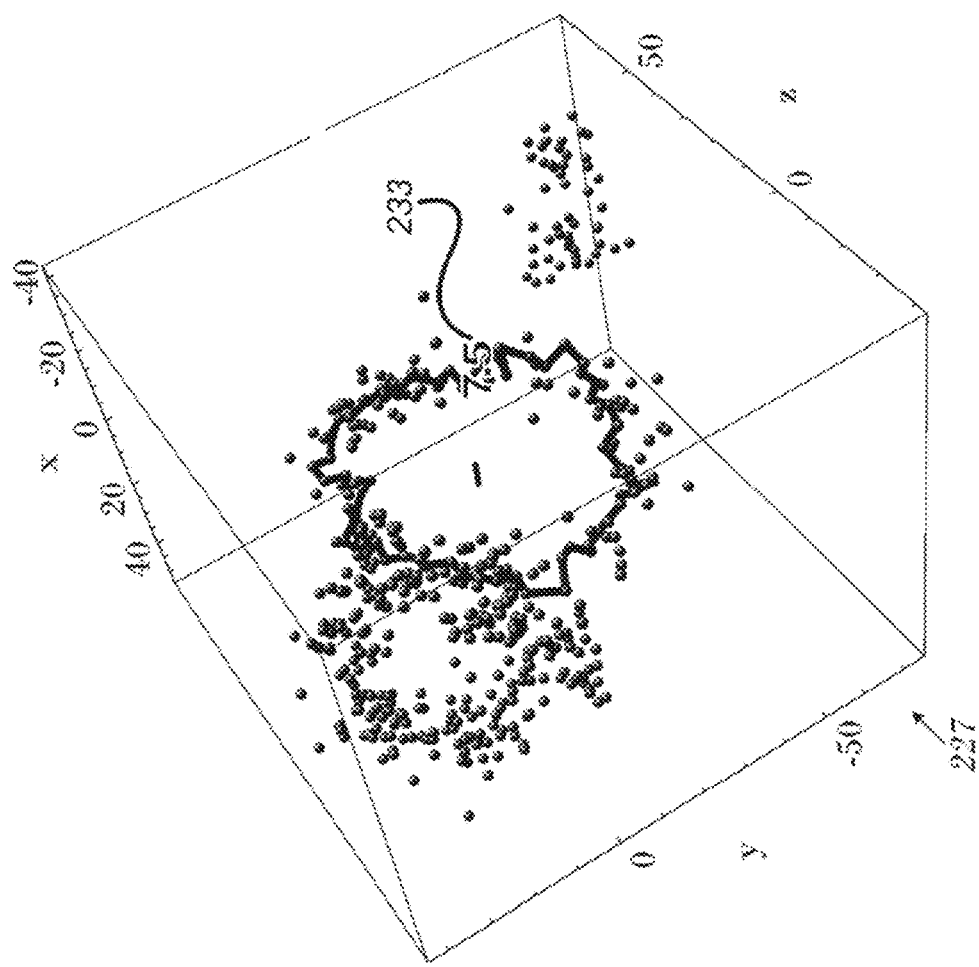
FIG. 19

PULMONARY VEIN ISOLATION GAP FINDER

CROSS-REFERENCE TO RELATED APPLICATIONS

This Application claims the benefit of U.S. Provisional Application No. 62/252,109, filed 6 Nov. 2015, which is herein incorporated by reference.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to medical instrumentation for tissue ablation. More particularly, this invention relates to treating cardiac arrhythmias by ablating in a vicinity of pulmonary venous tissue.

2. Description of the Related Art

It is now well-known that atrial fibrillation can be triggered by aberrant conduction pathways that originate in muscle bundles that extend from the atrium to the pulmonary veins and that ablation in order to produce electrical pulmonary vein isolation ablation can maintain sinus rhythm.

Contact force methods are effective in accomplishing circumferential pulmonary vein isolation. For example, commonly assigned U.S. Pat. No. 6,997,924 to Schwartz et al, which is herein incorporated by reference, describes pulmonary vein isolation using high energy emission of laser light energy. After transseptal advancement of a catheter to the ostium of a pulmonary vein, an anchoring balloon is expanded to position a mirror near the ostium of the pulmonary vein, such that light energy is reflected and directed circumferentially around the ostium of the pulmonary vein when a laser light source is energized. A circumferential ablation lesion is thereby produced, which effectively blocks electrical propagation between the pulmonary vein and the left atrium.

More recently hybrid catheters having contact force sensors and location sensors have been employed to isolate the pulmonary veins electrically, such as the Smart Touch™ catheter. However, residual conduction gaps may remain in some patients despite optimal ablation.

SUMMARY OF THE INVENTION

There is provided according to embodiments of the invention a method, which is carried out by ablating a plurality of sites in a heart of a living subject, projecting the locations of the sites in a 3-dimensional coordinate system onto a simulation plane, identifying a set of shortest 3-dimensional paths that correspond to 2-dimensional connections between pairs of the projected locations of the sites, and reporting a gap as a longest one of the set.

Yet another aspect of the method which is carried out by defining a source and a destination, projecting the source and the destination onto the simulation plane. The projected locations of the sites lie between the projected source and the projected destination on the simulation plane. The method is further carried out by randomly generating 2-dimensional paths on the simulation plane extending from the projected source to the projected destination, with passages between two of the projected locations of sites. The method is further carried out by determining a minimum size of the passages for each of the 2-dimensional paths, and reporting the largest minimum size of the 2-dimensional paths.

In still another aspect of the method the projected locations of the sites lie on an ellipse of best fit, wherein a portion of the projected locations of the sites lie outside the ellipse. The method is further carried out by enlarging the ellipse to include all of the projected locations of the sites.

An additional aspect of the method is carried out by modeling a portion of the heart as a triangular mesh including ablation points, and from the mesh nodes preparing a grid graph of graph nodes that are connected by undirected edges, representing the ablation points on the grid graph as corresponding graph nodes of the nearest mesh node thereof, and using the corresponding graph nodes as the projected locations of the sites to generate 2-dimensional paths.

There is further provided according to embodiments of the invention a method, which is carried out by ablating a plurality of sites in a heart of a living subject, and building a tree graph from all of the 3-dimensional locations of the sites. The method is further carried out by defining a path constructed of shortest segments between pairs of the sites, selecting a source, wherein the tree graph has a loop that winds about the source, the loop describing a gap between two of the ablation sites. The method is further carried out by reporting a shortest edge in the tree graph that can close the gap.

Another aspect of the method includes selecting additional sources and iterating the step of building a tree graph using the additional sources.

There is further provided according to embodiments of the invention an apparatus, including a probe adapted for insertion into contact with a heart in a body of a subject. The probe has a location sensor and an electrode on a distal portion of the probe, an ablation power generator, a processor linked to the location sensor, and arranged cooperatively with the ablation power generator for ablating a plurality of sites in the heart. The processor is operative for projecting the locations of the sites onto a simulation plane, identifying a set of shortest 3-dimensional paths that correspond to 2-dimensional connections between pairs of the projected locations of the sites, and reporting a gap as a longest one of the 3-dimensional paths.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein:

FIG. 15 is a graph illustrating another aspect of the method shown in FIG. 13 in accordance with an embodiment of the invention;

FIG. 19 is a composite screen display that was produced in accordance with an embodiment of the invention.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Definitions.

Discrete contour: a set of geodesic segments in a curved 2-dimensional space that form a closed curve.

Contour gap: the longest segment in a discrete contour.

Contour vertices: spheres between a pair of segments. The spheres can have finite radii.

Segment length: the Euclidean or geodesic distance between the vertices' centers minus the vertices' radii.

Isolation: a surface that prevents current flow from a source to a destination. If the current propagates in 2-dimensional space (e.g., a plane or the tissue of an atria) then isolation is a contour. If multiple possible surfaces exist, an isolating test should be defined for comparison. If the hindrance of the current flow through a slit, i.e., a gap between two vertices, decreases with the gap width, an isolating test could be constructed so that the discrete contour with the smallest gap becomes the isolation.

Winding number of a closed curve: the number of times a closed curve in a 2-dimensional curved space, winds about a predefined point source.

Current flow path: an open curve from a current source to a current destination.

Path contour segment intersection: a point where a closed contour intersects a current flow path.

System Overview.

Figure 1:
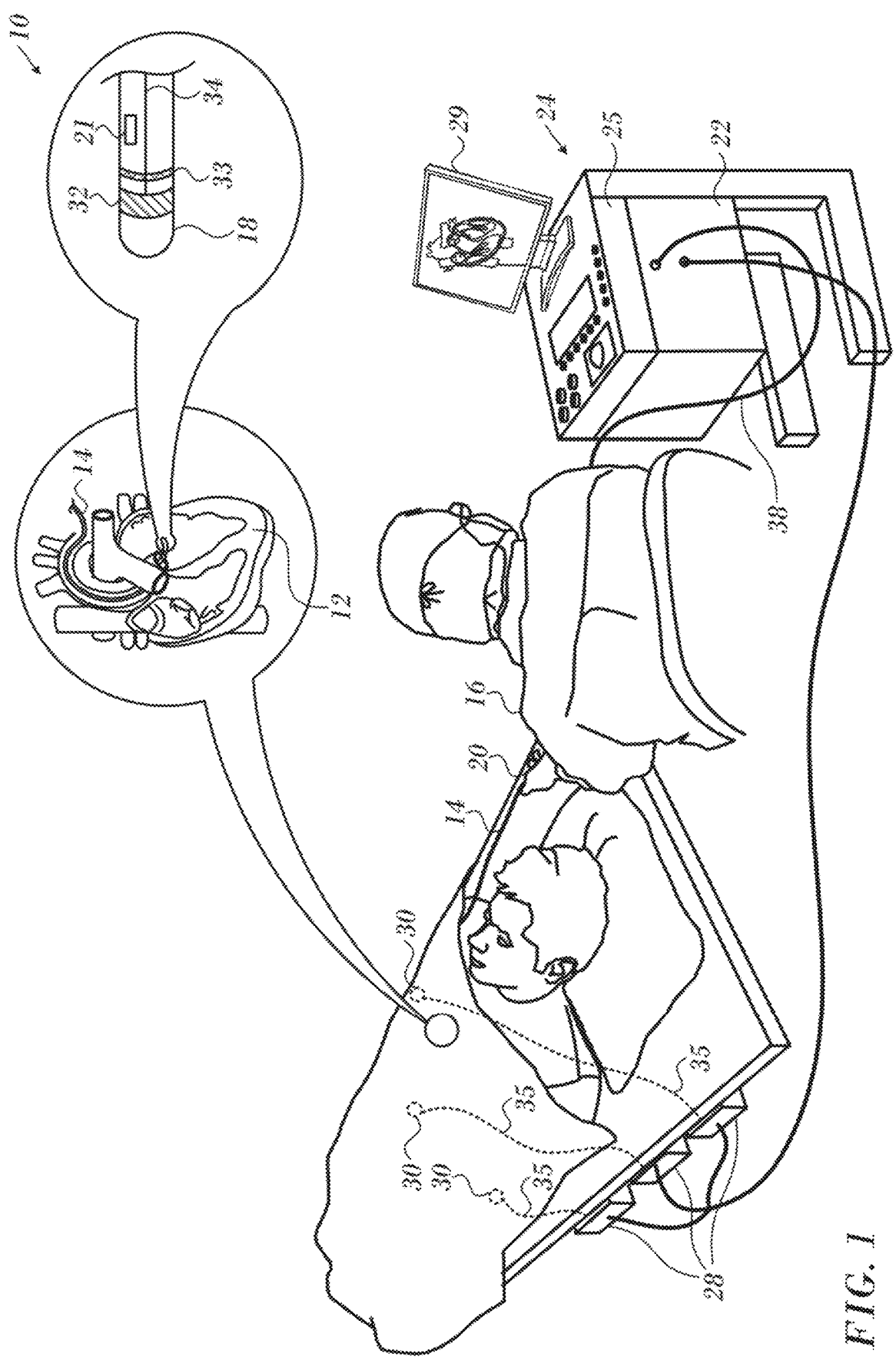
FIG. 1 is a pictorial illustration of a system for performing catheterization procedures on a heart, in accordance with a disclosed embodiment of the invention.

Turning now to the drawings, reference is initially made to FIG. 1, which is a pictorial illustration of a system 10 for evaluating electrical activity and performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 60° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 typically contains at least one position sensor 21 that provide signals to a processor 22, located in a console 24. The position sensors 21 may be a magnetic sensor or an electrode for an impedance-based locating system, as taught in U.S. Pat. No. 7,536,218, issued to Govari et al., which is herein incorporated by reference. The processor 22 may fulfill several processing functions as described below.

Ablation energy and electrical signals can be conveyed to and from the heart 12 through one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24 are disposed between the ablation electrodes 32 and have connections to the cable 34.

Wire connections 35 link the console 24 with body surface electrodes 30 and other components of a positioning sub-system for measuring location and orientation coordinates of the catheter 14. The processor 22 or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem is described in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by sensors such as electrical, temperature and contact force sensors, and a plurality of location sensing electrodes (not shown) located distally in the catheter 14. The digitized signals are received and used by the console 24 and the positioning system to compute the position and orientation of the catheter 14, and to analyze the electrical signals from the electrodes.

In order to generate electroanatomic maps, the processor 22 typically comprises an electroanatomic map generator, an image registration program, an image or data analysis program and a graphical user interface configured to present graphical information on the monitor 29.

Typically, the system 10 includes other elements, which are not shown in the figures for the sake of simplicity. For example, the system 10 may include an electrocardiogram (ECG) monitor, coupled to receive signals from one or more body surface electrodes, in order to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided. The system 10 may receive image data from an external imaging modality, such as an MRI unit or the like and includes image processors that can be incorporated in or invoked by the processor 22 for generating and displaying images.

It is desired that the lesions produced by the applications form a continuous line, so as to block electrical propagation thereacross. The procedures described below analyze the relationships among the lesions to determine whether significant gaps in the line exist. It should be noted that ablations sites exist in 3-dimensional space, but the presentation on a display represents a projection of three dimensions onto another surface, typically a 2-dimensional plane. Human evaluation of the display is possible, for example by repeated inspection using image rotation techniques, but is tedious and error-prone because of superposition of the spheres, e.g., a gap could be missed by the human operator, which could result in recurrence of the arrhythmia or even complete failure of the procedure. Operator-performance of this task invariably increases the duration of the catheterization session and hence the risk to the patient, and furthermore may limit the number of patients who can be evaluated in the catheterization laboratory One method of recording information concerning ablation sites is the VisiTag™ module, which is a component of the above-noted CARTO system.

The following summarizes two methods of finding the isolation, which are presented in detail in the embodiments below.

First Method.
(a) Generate all possible current flow paths. Since this isn't really possible, randomly generate a very large number of paths that can simulate the entire flow.
(b) For each path, find all intersecting segments and select the segment with the smallest segment length. Add these segments to a list of candidates.
(c) The segment with the largest segment length in the list is the largest gap in the isolation.
(d) The rest of the isolation curve can be found by elimination of curves that do not have the largest gap and trimming the list accordingly.

Second Method.
(a). Find the discrete contour constructed from the smallest segments that winds around a source only once.

First Embodiment

"No Map File" Variant.

Since an electric wave travels on the tissue surface, the wave's propagation and percolation can be simulated as a randomly propagating 1-dimensional wavefront. The simulation involves a random generation of multiple paths from the suspected source (the pulmonary veins) to the destination. The destination is a point on a closed contour comprising the tissue surface, and is beyond all sites of ablation. In other words, the line of ablation lies between the source and the destination. Each path comprises a series of steps from one intermediate point to the next until the destination is reached.

This variant does not rely on the existence of a map file describing the geometry of the atria.

Beginning at the source, the length and direction of each step of a path are randomly generated until the path reaches the destination. Propagation along such a path is treated as being hindered by the smallest gap between ablation sites in the path. The width of this gap is stored as the "blocking value" of the path.

If enough paths are generated, all plausible gaps will be traversed and mapped. The largest blocking value among the paths is reported as the size of the gap.

Each ablation site corresponds to a record in a database, for example, the above-noted VisiTag module. A variety of data is contained in each record, including the 3-dimensional coordinates of the site, contact force, duration of power application, and other information not relevant to this disclosure.

The procedure described below is particularly efficient if a source and destination of the paths to be generated are provided by the operator. However, as explained below in the discussion of FIG. 5, it is possible to estimate the source and destination automatically at some cost in accuracy. In cases where ablation dimensions are provided, they can be accounted for in the gap calculations.

Figure 2:
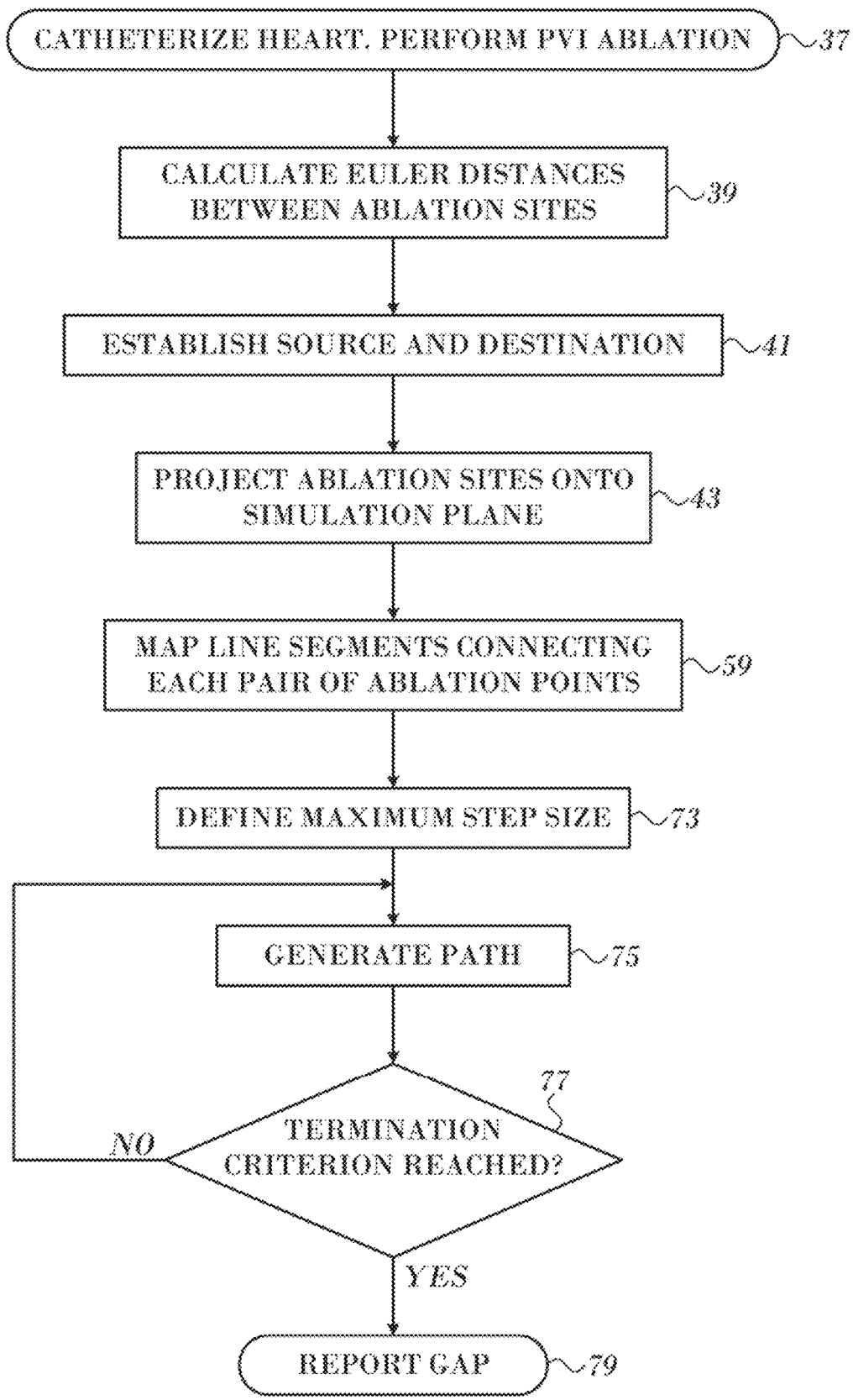
FIG. 2 is a flow chart of a method of determining a gap in an ablated region of tissue, in accordance with an embodiment of the invention.

Reference is now made to FIG. 2, which is a flow chart of a method of determining a gap in an ablated region of tissue, in accordance with an embodiment of the invention. The process steps are shown in a particular linear sequence in this and other flowcharts herein for clarity of presentation. However, it will be evident that many of them can be performed in parallel, asynchronously, or in different orders. Those skilled in the art will also appreciate that a process could alternatively be represented as a number of interrelated states or events, e.g., in a state diagram. Moreover, not all illustrated process steps may be required to implement the method. The method is described in reference to the example of pulmonary vein isolation; however it is applicable to other ablation procedures in the heart.

At initial step 37 the subject is catheterized, and a series of ablations at respective sites is performed, typically, the ablations effect isolation of a pulmonary vein (PVI). Data relevant to each ablation site is memorized as noted above. The operator may be presented with a display illustrating the sites and data pertaining to the ablations.

Next, at step 39 the Euler distances between all pairs of ablation sites are calculated. It will be recalled that the 3-dimensional coordinates of the sites can be determined using the position sensor 21 (FIG. 1). Alternatively, the radii of the lesions created at the sites may be predicted using known methods and taken into consideration for the distance computation. This of course reduces the effective distances between the pair.

Next, at step 41 the source and destination for the paths are established. The paths are projected onto a canonical ellipse, whose parameters are obtained in variants of step 41, which are described below. The plane of the ellipse is referred to herein as a "simulation plane".

Figure 3:
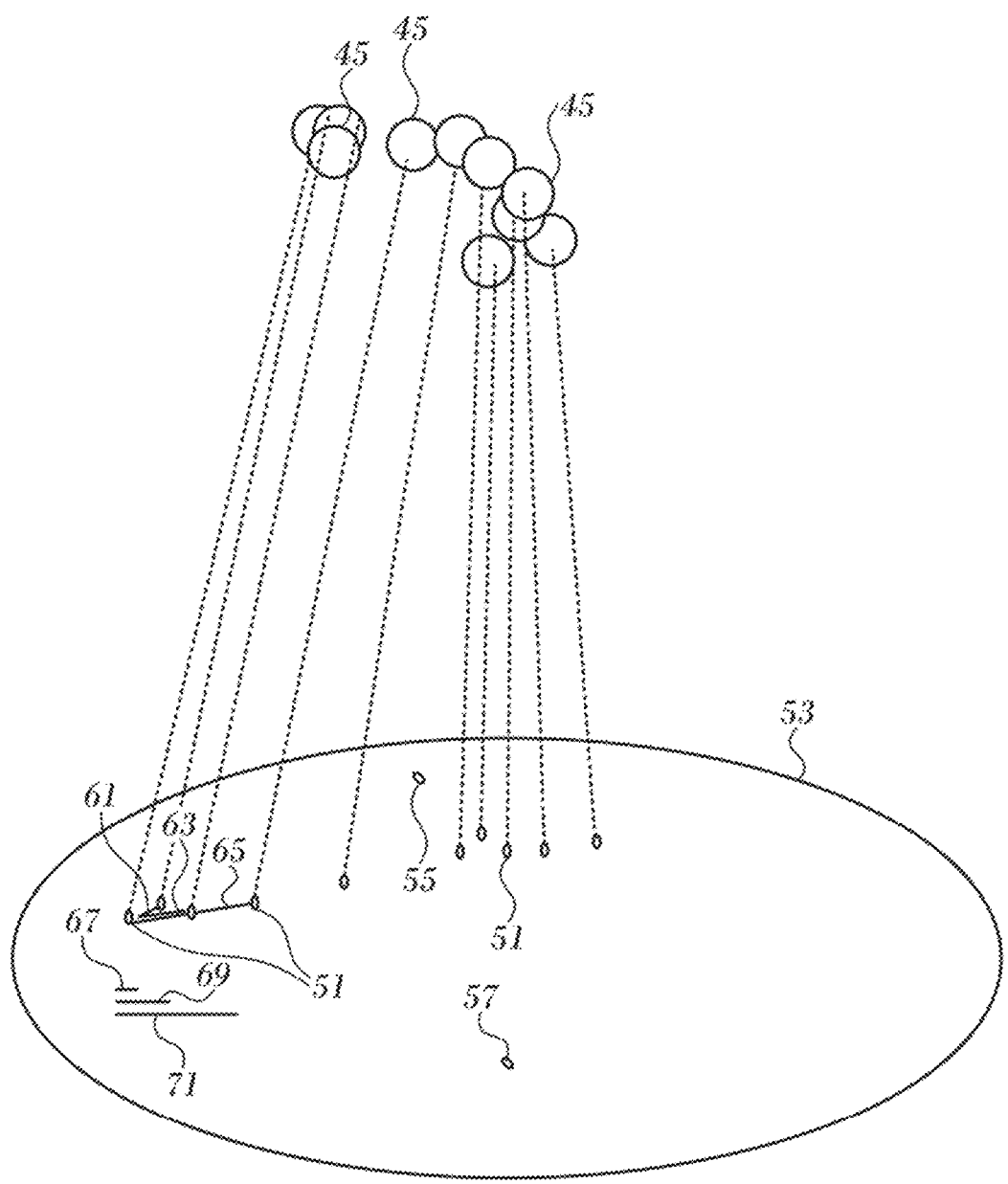
FIG. 3 is a graphical illustration of an aspect of the method described in FIG. 2 in accordance with an embodiment of the invention.

Next, at step 43, using the 3-dimensional spatial coordinates of the ablation sites, the points of ablation are transformed onto the simulation plane. Reference is now made to FIG. 3, which is a graphical illustration of the procedure described in step 43 in accordance with an embodiment of the invention. A subset of ablation points 45 is illustrated for simplicity. The 2-dimensional projection of the ablation points 45 appears as a series of transformed ablation points 51 that lie within the bounds of an ellipse 53. Source 55 and destination 57 are indicated. Sites of energy application, typically radiofrequency energy, are represented by three color-coded categories of the ablation points 45, as indicated by different hatched patterns. While three categories are indicated on FIG. 3 for convenience of presentation, many gradations may be color-coded and presented on a suitable display monitor. The gradations may indicate levels of power intensity. From this and other memorized information concerning the ablation site, such as duration of power application, and contact force, it is possible to predict the diameter of the lesions created, for example from the teachings of commonly assigned U.S. Patent Application Publication No. 20140100563 by Govari et al., which is herein incorporated by reference.

At step 59 (FIG. 2) the points 51 are chosen pairwise, and line segments defined by each pair are mapped. For example, the pairs 61, 63, 65 map to line segments 67, 69, 71, respectively, The lengths of the line segments 67, 69, 71 reflect the Euler distances between the pairs 61, 63, 65.

Reverting to FIG. 2, at step 73 a maximum step size (stepMax) is determined. This may be calculated by dividing the longest distance between ablation sites by a user-configured value, e.g., 20. This value affects convergence of the simulation.

Next, at step 75 a path is generated, as described below. Step 75 is performed iteratively. Associated with each path created by a performance of step 75 is a minimum blocking value, i.e., the Euler distance of a line segment connecting two ablation points and crossed by the path.

Next, at decision step 77, it is determined if a termination criterion for the iteration of step 75 has been reached. For example, the criterion can be a predetermined number of iterations, the expiration of a time interval, or a combination thereof. If the determination at decision step 77 is negative, then control returns to step 75.

If the determination at decision step 77 is affirmative, then control proceeds to final step 79. A gap in the ablation points is reported as the largest of the minimum block lengths found in the paths generated in step 75.

Figure 4:
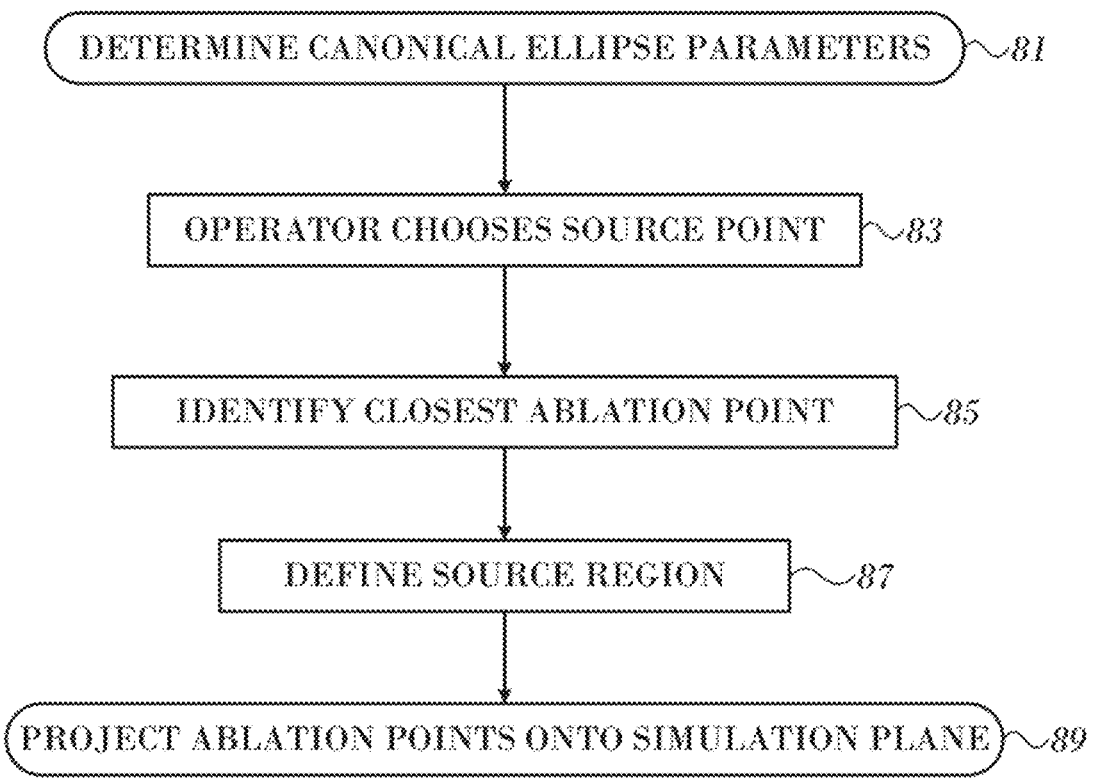
FIG. 4 is a flow chart of a method of establishing the source and destination of a path in accordance with an embodiment of the invention.

Reference is now made to FIG. 4, which is a flow chart of one method of establishing the source and destination (step 41; FIG. 2) in accordance with an embodiment of the invention. Parameters of the canonical ellipse are obtained at initial step 81 using the least squares of the distance residuals (measured from a site position obtained from the canonical ellipse equations). Alternatively, the parameters may be obtained by taking the singular value decomposition of all sites, which affects the three radii of an ellipsoid that can be generated from the canonical ellipse. The two larger radii span a plane. These techniques are known in the art and are not further discussed herein.

Next, at step 83 a source point for a conduction path is determined by an operator. The source point may be chosen using a graphical user interface, for example by a mouse click on a screen display.

Next, at step 85 the 2-dimensional projection of the ablation point closest to the source point chosen in initial step 81 is identified. Using this point minimizes computation time.

Next, at step 87 a source region is defined on the simulation plane about the source point as a circle centered on the source point and having a radius equal to the distance from the source point to the ablation point identified in step 85.

Then, at final step 89, the other ablation points are projected onto the simulation plane.

Figure 5:
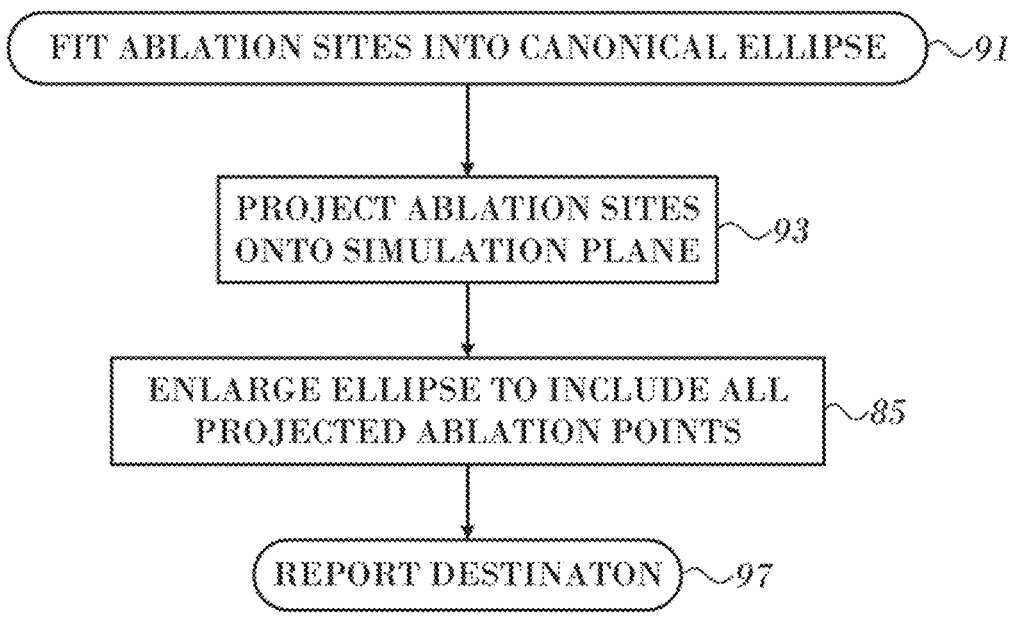
FIG. 5 is a flow chart of a method of establishing the source and destination of a path in accordance with an alternate embodiment of the invention.

Reference is now made to FIG. 5, which is a flow chart of another method of performing step 41 (FIG. 2), in accordance with an embodiment of the invention. In this variant the source and destination are estimated automatically.

In initial step 91 the ablation sites are fitted into the canonical ellipse, which is established as described above with respect to initial step 81 (FIG. 4) to define the simulation plane. The ellipse of best fit may not include all the ablation points, but should include the majority of them.

Next, at step 93 the ablation points are projected onto the simulation plane.

Next, at step 95, keeping its aspect ratio constant, the ellipse defined and fitted in initial step 91 is enlarged to include all the projected ablation points Then, at final step 97, the ellipse resulting from step 95 is reported as the destination for the paths.

Figure 6:
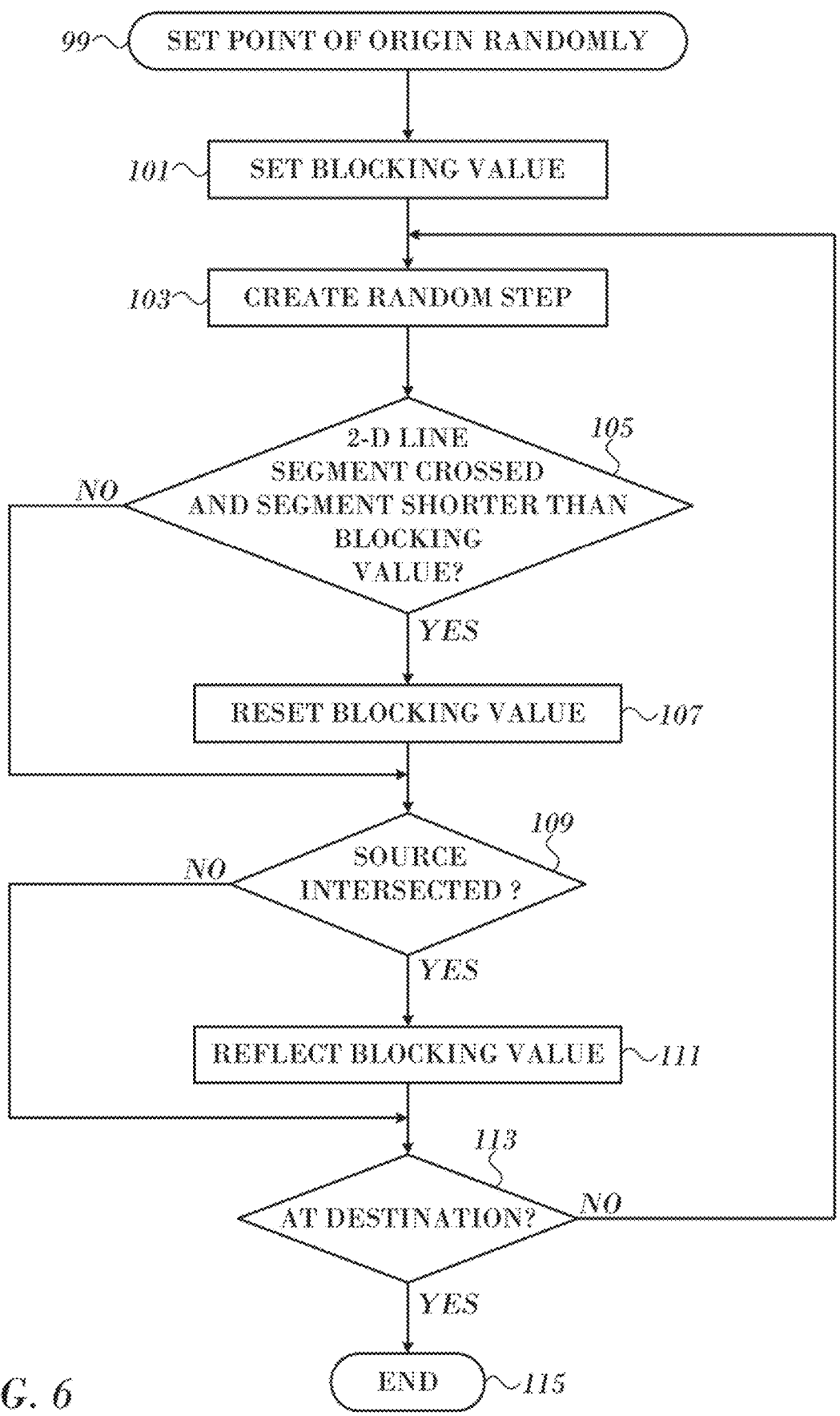
FIG. 6 is a flow chart of a method of path generation in accordance with an embodiment of the invention.

Reference is now made to FIG. 6, which is a flow chart detailing path generation (step 75; FIG. 2), in accordance with an embodiment of the invention. At initial step 99 a suitably limited random number is generated. This number represents an angle between from 0 to 360 degrees and designates a point of origin for the path on the contour of the source, usually a circle or ellipse.

Next, at step 101 a current blocking value is set. This is initialized to the largest real number that can be represented in the processor.

Next, at step 103 a step is created, having with a length (r) and direction ($\theta$) determined randomly (r~Uniform[0; step-Max], $\theta$~Uniform[0; 2$\pi$]).

Next, at decision step 105, it is determined if on the simulation plane (1) the step crosses a 2-dimensional line segment that connects a pair of projected ablation sites and (2) the 3-dimensional Euler distance between that pair is smaller than the current blocking value.

If the determination at decision step 105 is affirmative, then control proceeds to step 107. The current blocking value is reset to the 3-dimensional Euler distance between the pair.

After performing step 107 or if the determination at decision step 105 is negative, at decision step 109 it is determined if the path has intersected the source.

If the determination at decision step 109 is affirmative, then at step 111 the path is reflected at an angle ($\theta_r$) according to its angle of incidence ($\theta_i$) on the source ($\theta_r=\theta_i$). When the source is a point, reflection is not required.

After performing step 111 or if the determination at decision step 109 is negative, at decision step 113, it is determined if the destination has been reached. If the determination is negative, then control returns to step 103 to create another random step.

If the determination at decision step 113 is affirmative, then the procedure ends at final step 115.

Map File Variant.

This variant is used when a map file, i.e., a mesh file, exists as a map of the atria. Such files can be generated, for example, using the teachings of U.S. Patent Application Publication No. 20140125653, entitled Combining Three-Dimensional Surfaces, U.S. Pat. No. 9,265,434, entitled Dynamic Feature Rich Anatomical Reconstruction from a Point Cloud and U.S. Patent Application Publication No. 20150018698, entitled Model Based Reconstruction of the Heart from Sparse Samples, all of which are commonly assigned and herein incorporated by reference. Ablation points as shown in FIG. 3 are available for this variant.

Figure 7:
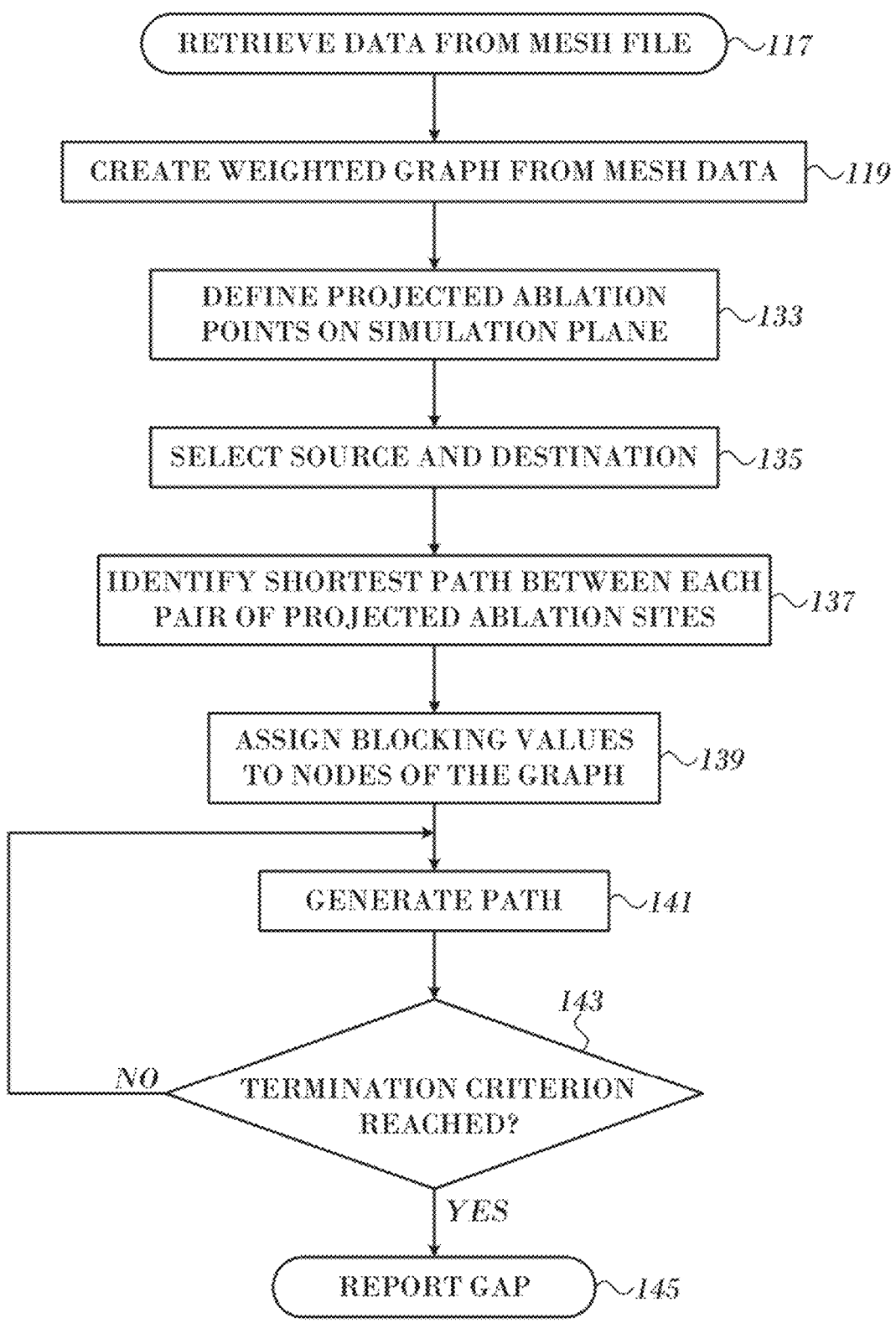
FIG. 7 is a flow chart of a method of determining a gap in an ablated region of tissue in accordance with an alternate embodiment of the invention.

Reference is now made to FIG. 7, which is a flow chart of a method of determining a gap in an ablated region of tissue, in accordance with an alternate embodiment of the invention. Triangle vertices and indices are retrieved from the mesh file at initial step 117 and used as graph nodes. The graphs produced in this variant are referred to as "grid graphs", by which they may be distinguished from "tree graphs" and other configurations discussed elsewhere herein. While the vertices are defined as a mesh in 3-dimensional space, the nodes are defined in an abstract topological space.

Next, at step 119 a weighted grid graph with nodes and undirected edges is prepared. The graph is weighted according to the 3-dimensional Euler distances between neighboring vertices.

Figure 8:
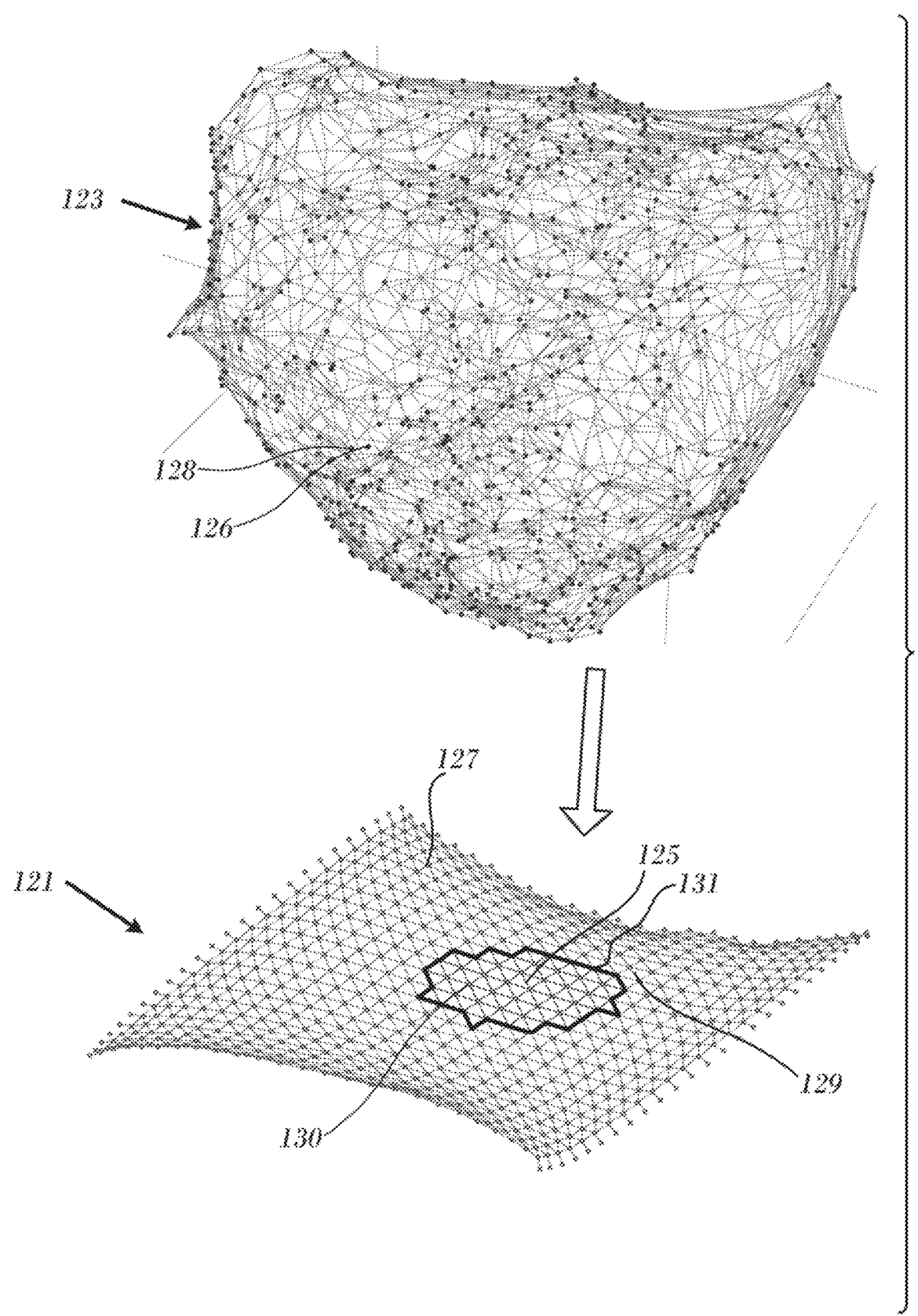
FIG. 8 illustrates a weighted graph prepared from a 3-dimensional mesh in accordance with an embodiment of the invention.

Reference is now made to FIG. 8, which illustrates a weighted grid graph 121 prepared according to step 119 (FIG. 7) from a 3-dimensional mesh 123, in accordance with an embodiment of the invention. Portions of the grid graph 121 are referred to as sub-graphs, e.g., sub-graph 125 is a sub-graph of grid graph 121. The grid graph 121 comprises bulk nodes, which include nodes of the sub-graph 125 and nodes 127 that are outside the sub-graph 125. Sub-graph 125 also comprises sub-graph bulk nodes, which are entirely within the sub-graph 125 and are connected only to other nodes of the sub-graph 125. The grid graph 121 also comprises nodes 129 that are in contact with surface nodes of the sub-graph 125, e.g., node 131. As will be seen from the discussion below, bulk nodes of the source, e.g., sub-graph 125 can be removed to simplify the calculation and the surface nodes on the boundary, e.g., node 131, can be used as the first step in a simulated path.

Referring to FIG. 7 and to FIG. 8, ablation points that are modeled on the mesh 123, e.g., ablation point 126, may lie between nodes of the mesh 123. Such ablation points are not projected directly onto the grid graph 121, but at step 133 are treated as the projections of their nearest mesh vertices. Thus, a projection of node 128 (the node on the mesh 123 closest to the ablation point 126) onto the grid graph 121 as corresponding graph node 130 would represent ablation point 126 on the grid graph.

Next, at step 135 a source and a destination are selected by retrieval of the source by the operator. Alternatively the source and destination may be estimated. Details of step 135 are provided below.

Next, at step 137 paths on the simulation plane connecting each pair of projected ablation sites are identified. The length of the shortest 3-dimensional path between each pair of the projected ablation sites is determined for the connections. This step constitutes a solution to the shortest path problem. It is accomplished using a known algorithm, e.g., Dijkstra's algorithm, or several other known algorithms. The standard algorithm provided in Mathematica® is suitable for step 137. Alternatively, a "breadth-first" scan may be performed.

Next, at step 139 assign to each node a respective "blocking value". The blocking value corresponds to the shortest one of the paths developed in step 137 that passes through the node. If none of the paths passes through a node, its blocking value is treated as infinite.

Next, at step 141 a path is generated, as described below. Step 141 is performed iteratively. Associated with each path created by a performance of step 141 is a minimum blocking value, i.e., the Euler distance of a line segment connecting two ablation points and crossed by the path.

Next, at decision step 143 it is determined if a termination criterion for the iteration of step 141 has been reached. For example, this can be a predetermined number of iterations, or the expiration of a time interval, or a combination thereof. If the determination at decision step 143 is negative, then control returns to step 141.

If the determination at decision step 143 is affirmative, then control proceeds to final step 145. A gap in the ablation points is reported as the largest of the minimum blocking values found in the paths generated in the iterations of step 141.

Figure 9:
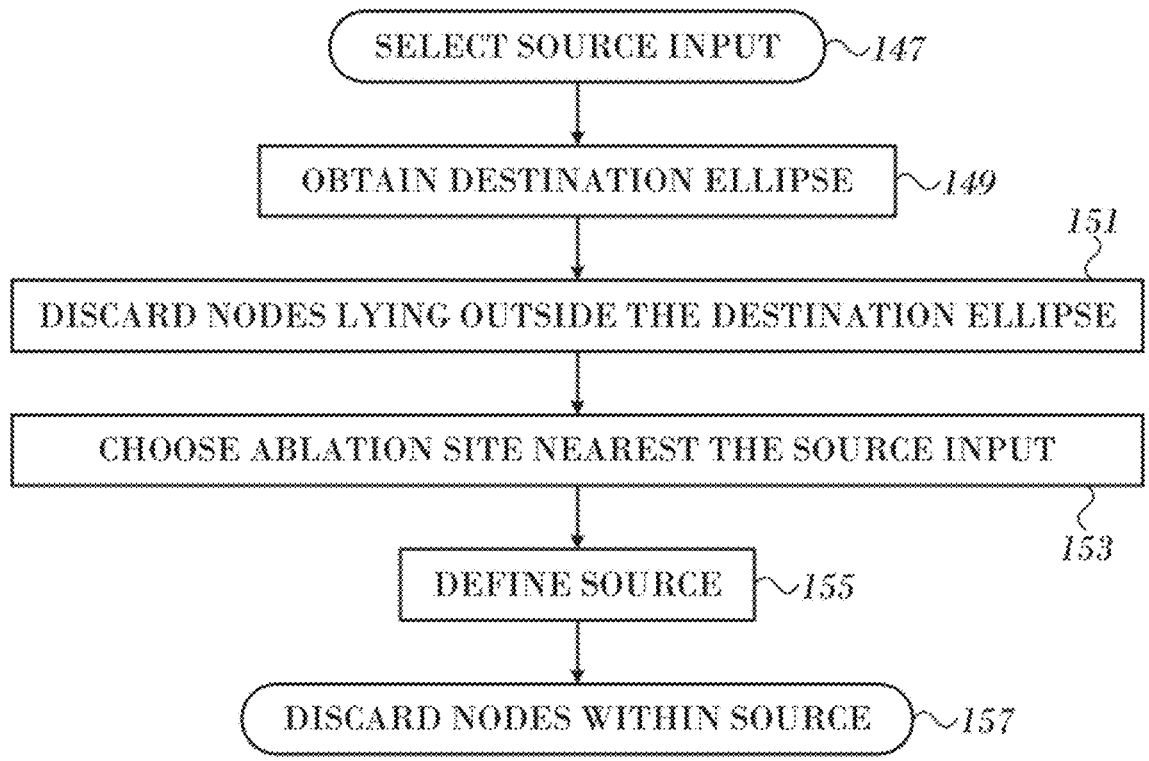
FIG. 9 is a detailed flow chart of an aspect of the method shown in FIG. 7 in accordance with an embodiment of the invention.

Reference is now made to FIG. 9, which is a detailed flow chart of the method of step 135 (FIG. 7) in accordance with an embodiment of the invention. The source and destination of a path are obtained by retrieval from the operator, in accordance with an embodiment of the invention.

At initial step 147 a source input and destination are chosen by the operator. Using a graphical user interface, the operator identifies a source point in 3-dimensional space, and draws a 2-dimensional ellipse to define the destination. Next, at step 149 a destination canonical ellipse parameter is obtained as described above, resulting in a 2-dimensional ellipse located in 3-dimensional space.

Next, at step 151 nodes of the grid graph prepared in step 119 having 3-dimensional coordinates that fall outside the ellipse are removed from the graph.

Next, at step 153 the ablation site nearest to the source input chosen in initial step 147 is identified.

Next, at step 155 the source is defined as the 1-dimensional surface of a sub-graph of the weighted graph generated in step 119 (FIG. 7) within the distance from the source input chosen at initial step 147 to the nearest projected ablation site.

Then, at final step 157 all bulk nodes from the weighted grid graph prepared in step 119 (FIG. 7), i.e., the sub-graph bulk nodes of the sub-graph 125 (FIG. 8) are removed from further consideration.

Figure 10:
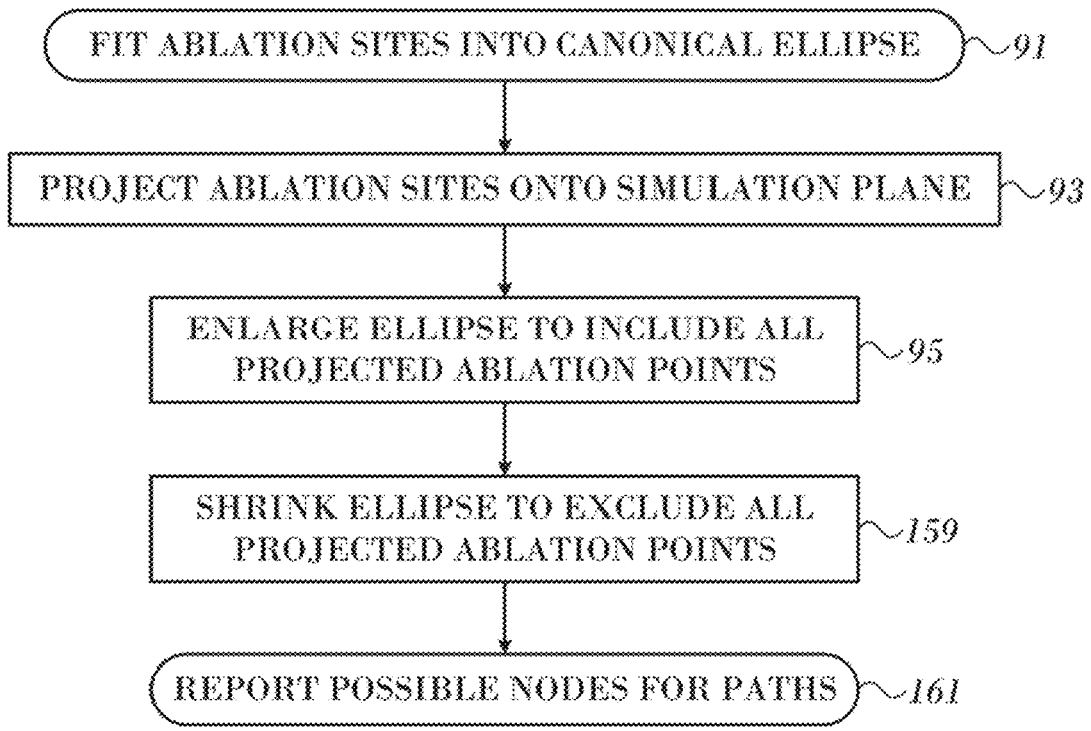
FIG. 10 is a detailed flow chart of an aspect of the method shown in FIG. 7 in accordance with an alternate embodiment of the invention.

Alternatively, the source and destination can be estimated using a modification of the method described above with respect to FIG. 5. Reference is now made to FIG. 10, which is a detailed flow chart of step 135 (FIG. 7) in accordance with an alternate embodiment of the invention. In this variant the source and destination are estimated automatically. Steps 91, 93, 95 are common to the method of FIG. 5 and are not re-described. Then, in step 159 the ellipse is shrunk to exclude all projected ablation points from its borders.

After performing step 159, in final step 161 only nodes from the weighted grid graph prepared in step 119 having 3-dimensional coordinates that project between the enlarged and shrunken ellipses (steps 95, 159) are retained for as possible nodes for use in path generation.

Figure 11:
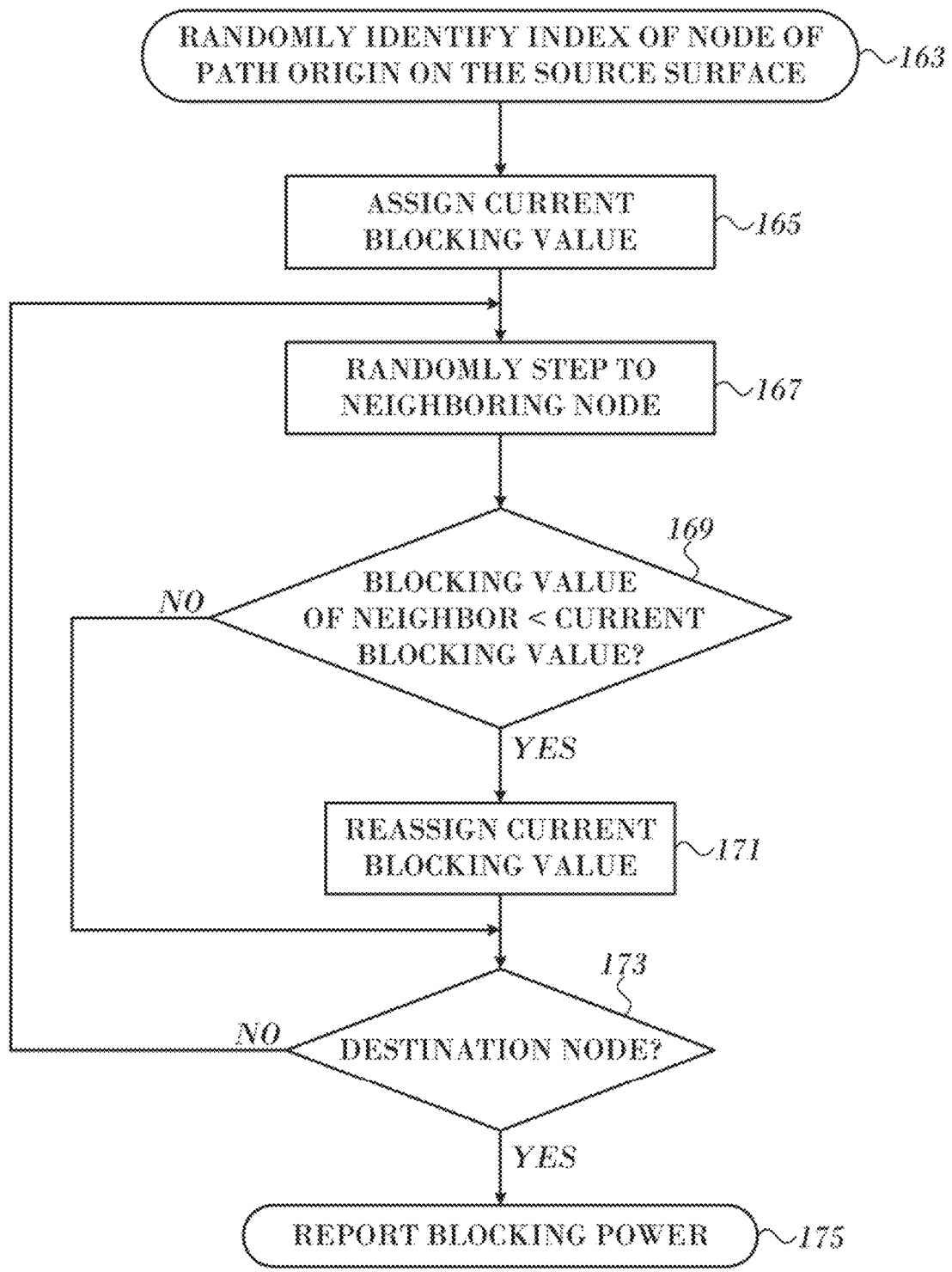
FIG. 11 is a flow chart detailing generation of a path according to the method shown in FIG. 7 in accordance with an embodiment of the invention.

Reference is now made to FIG. 11, which is a flow chart detailing generation of a path according to step 141 (FIG. 7), in accordance with an embodiment of the invention. Nodes are identified by index values, which are pointers to data objects describing the mesh. Otherwise, these index values have no physical significance. At initial step 163 A random number (Uniform[0; 2π]) is generated, and used as the index along the source's surface. The corresponding node of the mesh file becomes the origin of the path.

Next, at step 165 the blocking value of the node selected in initial step 163 is assigned as the current blocking value of the path.

Next, at step 167 a step of the path is generated. The step leads to a randomly selected neighboring node. A node and a neighboring node are directly connected. The distance therebetween in abstract space is "1".

Next, at decision step 169, it is determined if the blocking value of the neighboring node selected in step 167 is less than the current blocking value. If the determination at decision step 169 is affirmative, then control proceeds to step 171. The current blocking value is reset to the blocking value of the neighboring node.

After performing step 171 or if the determination at decision step 169 is negative, then at decision step 173, it is determined if the neighboring node chosen in step 167 is a destination node.

If the determination at decision step 173 is negative, then control returns to step 167 to continue generation of the path.

If the determination at decision step 173 is affirmative, then at final step 175 the current blocking value is reported as the blocking value of the path.

Combined Variant.

Some aspects of the no-map variant can be used to improve the efficiency of computing the map file variant. Locations on the mesh that are far from the original ablation sites can be projected to the simulation plane and the nearest node can be selected according to the 2-dimensional Euler distances.

Second Embodiment

In this embodiment paths between the source and the destination are not calculated. Rather the gap is found from geometrical considerations. A tree graph is built so that paths between all sites have segments of minimal length.

Figure 12:
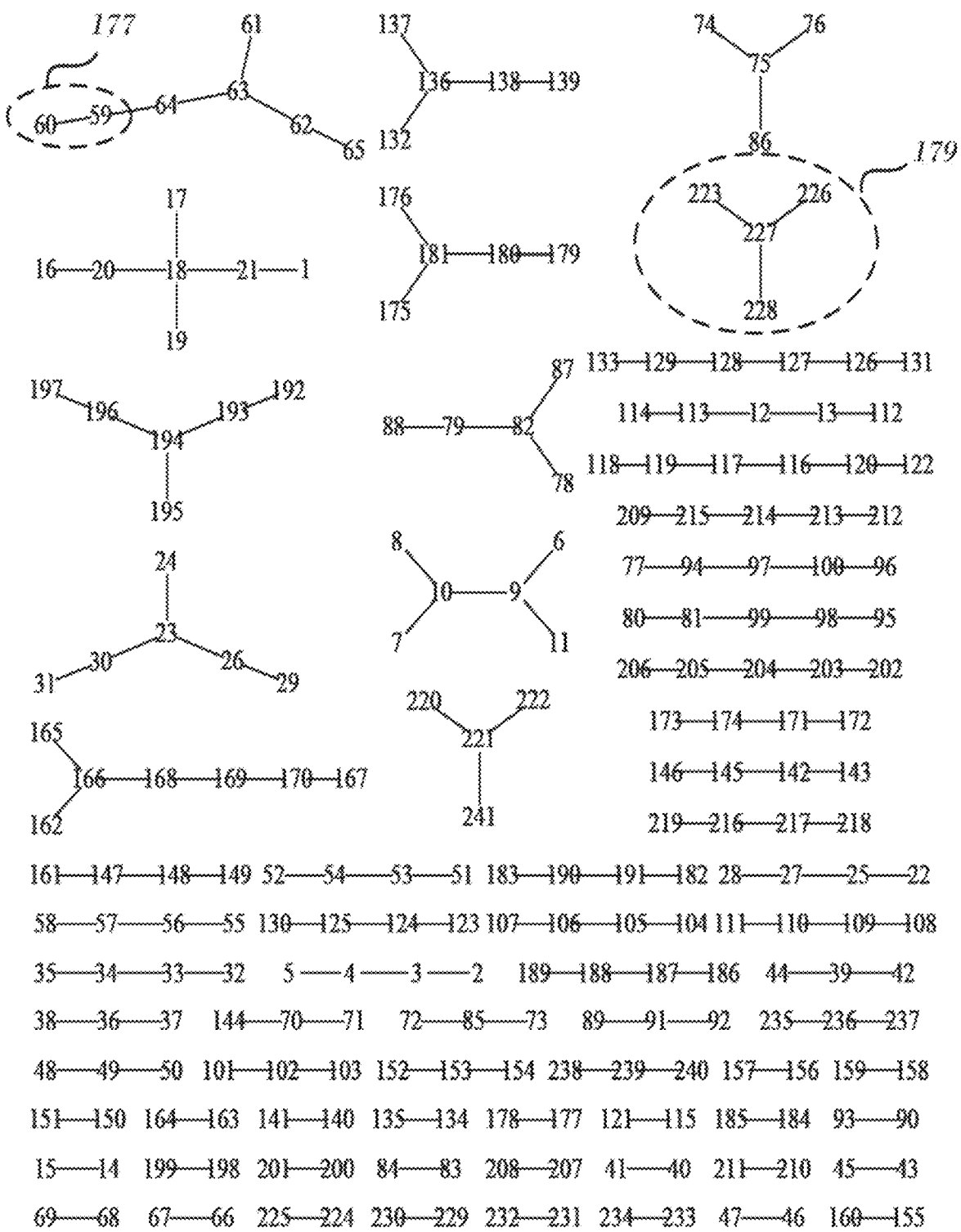
FIG. 12 is an exemplary graph of ablation sites in accordance with an embodiment of the invention.

Reference is now made to FIG. 12, which is an intermediate graph that is useful for constructing a tree graph of ablation sites in accordance with an embodiment of the invention. Nodes of the tree graph are identified by numbers, which are indices to data records of their associated ablation sites. A pair of ablation sites comprises a node connected to its nearest node by an edge. One pair 177 is delineated by a broken circle. A cluster 179 of nodes is outlined by a broken circle.

Figure 13:
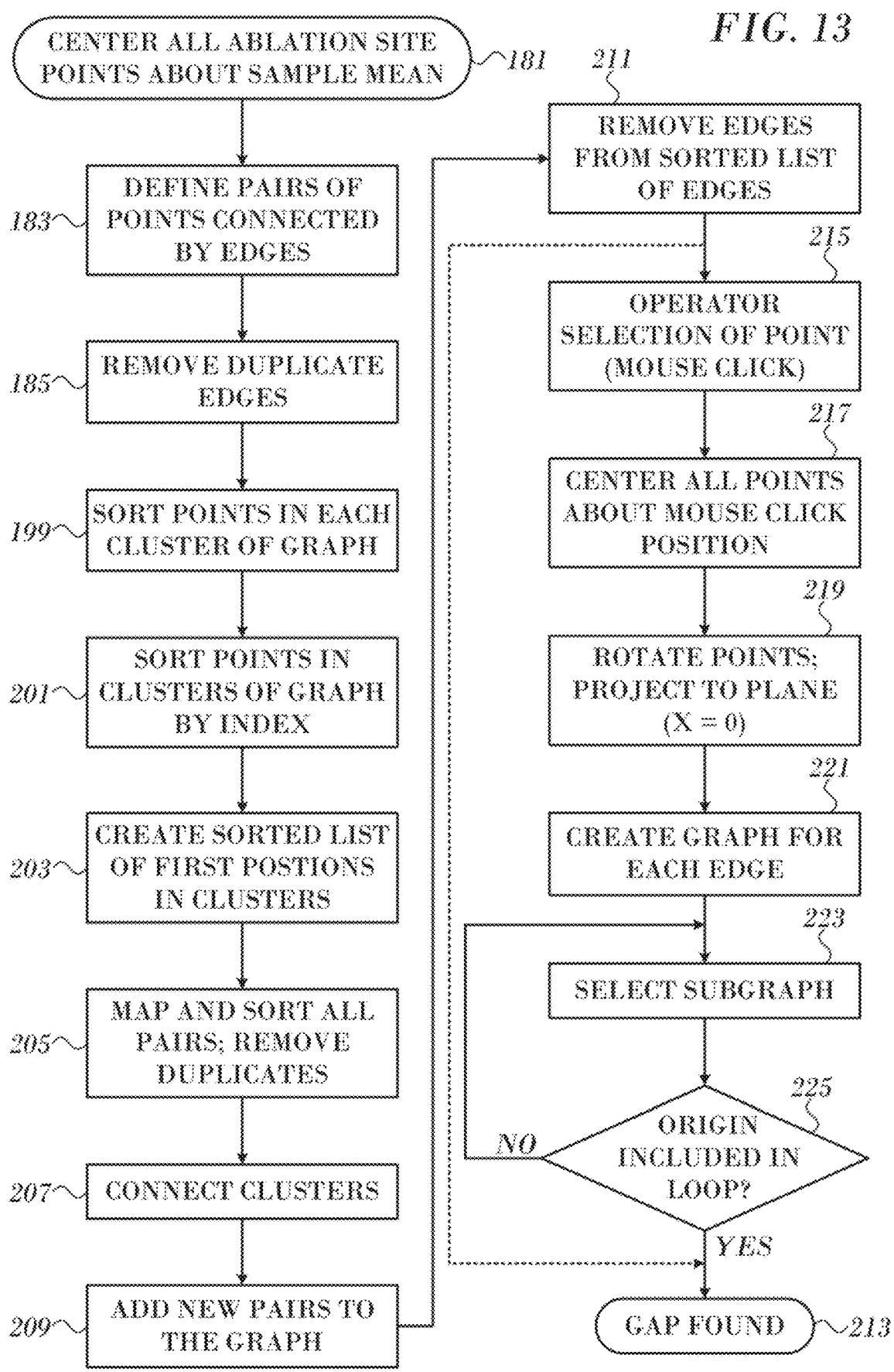
FIG. 13 is a flow chart of a method of path generation in accordance with an embodiment of the invention.

Reference is now made to FIG. 13, which is a flow chart of a method of path generation in accordance with an embodiment of the invention. The method finds a path necessary for isolating the source from the destination that has the smallest blocking value. The largest segment of the path is reported as the gap.

At initial step 181 a sample mean is identified, i.e., a mean of a set of position vectors of all the ablation sites, and the points are centered about the mean by subtracting the mean from each of the other vectors.

Next, at step 183 for each point, a pair is defined as a graph edge to the nearest other point. Two points may be found to be connected indirectly. All duplicate edges are removed at step 185. Implementations of initial step 181 and step 183 are detailed in the Mathematica code of Listing 1. Other listings herein are also expressed in Mathematica code.

Figure 14:
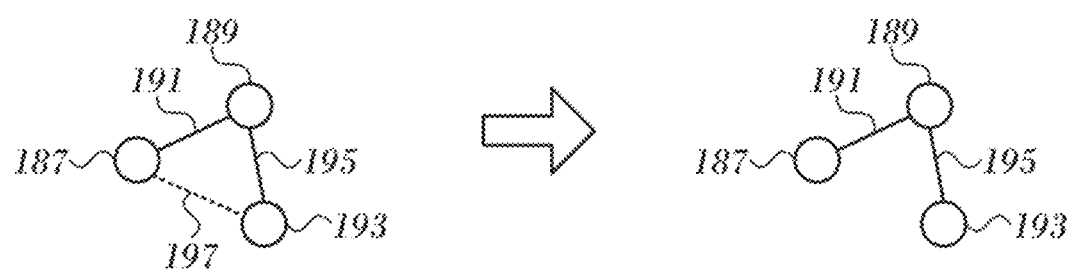
FIG. 14 is a graph illustrating an aspect of the method shown in FIG. 13 in accordance with an embodiment of the invention.

Listing 1 cent=Mean[dataSet];
centeredDataSet=#−cent &/@ dataSet;
NearestF=Nearest[centeredDataSet→Automatic];
firstgrdat=Union[UndirectedEdge @@ Sort@NearestF
  [#, 2] &/@ centeredDataSet];

Reference is now made to FIG. 14, which is a simplified graph illustrating step 185 (FIG. 13) in accordance with an embodiment of the invention. A point 187 is a nearest neighbor of point 189 (measured by the Euler 3-dimensional distance). The points 187, 189 are connected by edge 191. In like manner point 189 and point 193 form a pair connected by edge 195. Yet another pair comprises points 187, 193 connected by edge 197. However, edge 197 is redundant and is therefore deleted, as shown on the right side of the figure.

Reverting to FIG. 13, in the following steps a graph is constructed from all the edges remaining after performing step 185. Clusters are defined as connected components in the graph, for example, cluster 179 (FIG. 12).

At step 199 the points in each cluster are sorted by index. It will be recalled that the index is an arbitrary reference to a data object. When step 199 is complete the first point in the sorted cluster has the smallest index in that cluster.

Then at step 201 a list of clusters is sorted by the index of the first point within the clusters, so that the order of the clusters changes, as shown in Listing 2

Listing 2 firstcon=SortBy[Sort/@ ConnectedComponents[firstgr], First];

Next, at step 203 a sorted list of the first positions of each cluster is derived from the sorted list of clusters that was prepared in step 201 to identify each point with the identifier of the first point in its cluster, as shown in Listing 3.

Listing 3 firstList=Table[Position[firstcon, i, 2] [[1, 1]], {i, Sort@Flatten@firstcon}];

In step 205, all possible pairs of points are mapped and sorted according to the distances between members of the pairs to form a sorted list of all possible edges. Duplicates are then removed.

Step 207 comprises connecting the clusters by iteration over the sorted pairs. If indices of a pair relate to more than one cluster, the pair is retained and the two clusters are coalesced. The process is aborted when all points are in the same cluster.

Reference is now made to FIG. 15, which is a typical graph resulting from the performance of step 207 (FIG. 13) in accordance with an embodiment of the invention.

Next, at step 209 the graph of FIG. 15 is enlarged by forming a union with the intermediate graph of FIG. 12. The procedure is detailed in Listing 4.

Listing 4 pathdat=Union[firstgrdat, restgraphdat]
GraphUnion[firstgr, restgraph]

Figure 16:
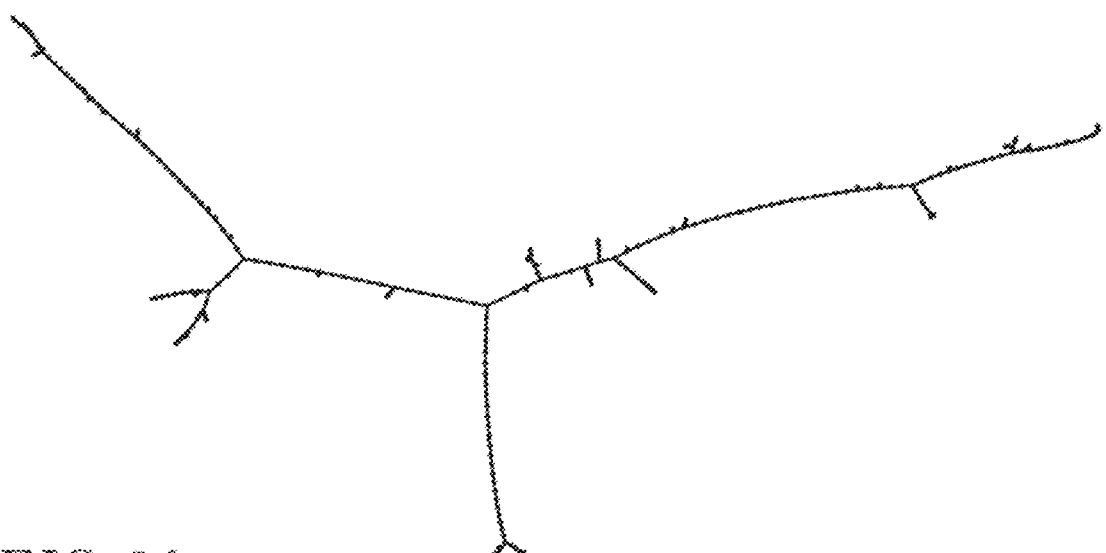
FIG. 16 is a tree graph resulting from the performance of a step the method shown in FIG. 13 in accordance with an embodiment of the invention.

Reference is now made to FIG. 16, which is a typical tree graph resulting from the performance of step 209 in accordance with an embodiment of the invention. The tree graph defines a path constructed of the shortest segments for each pair of points.

Figure 17:
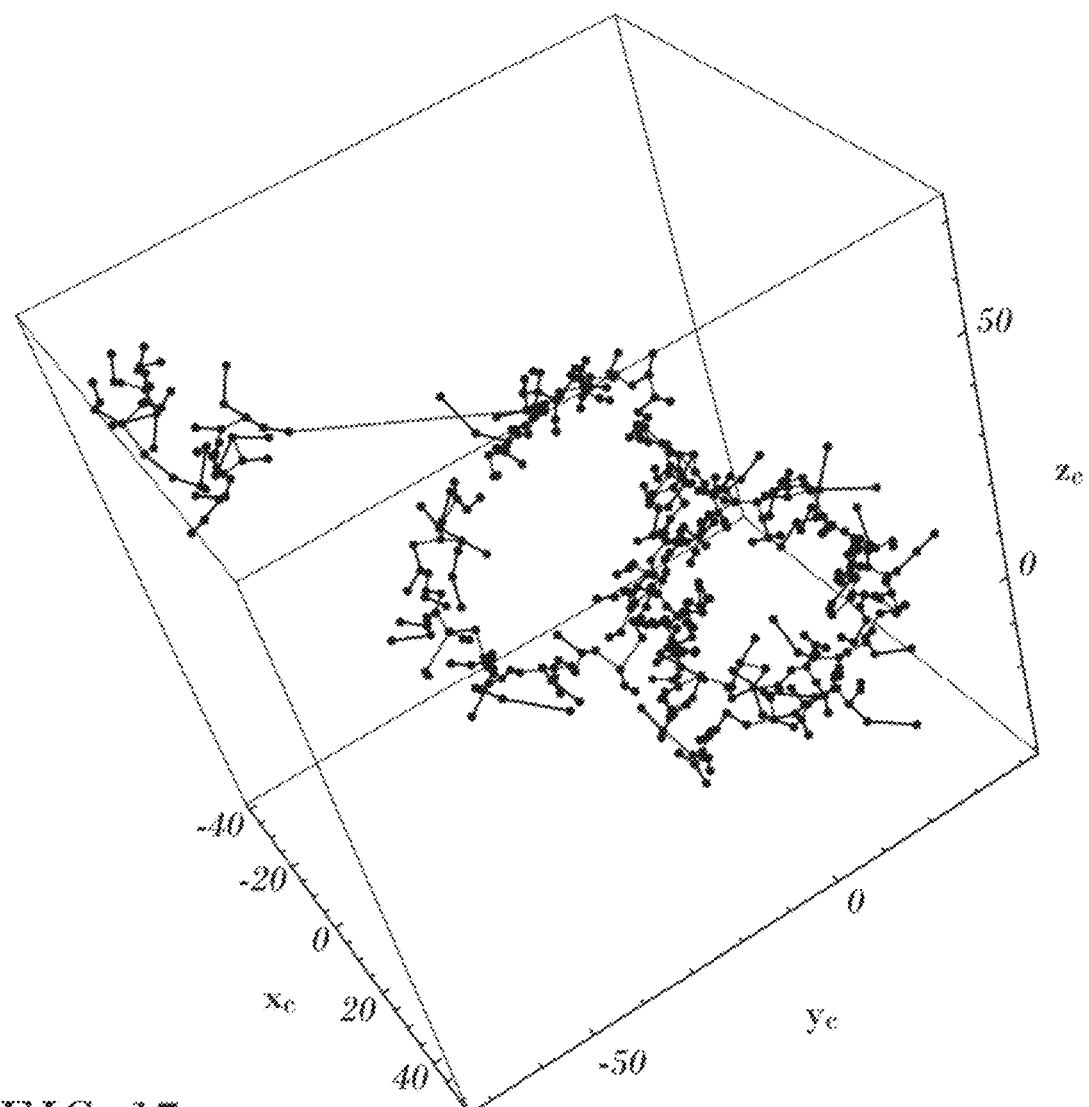
FIG. 17 is a 3-dimensional presentation of the points corresponding of the tree graph of FIG. 16 in accordance with an embodiment of the invention.

Reference is now made to FIG. 17, which is a 3-dimensional presentation of the points corresponding of the tree graph of FIG. 16, in accordance with an embodiment of the invention. FIG. 16 and FIG. 17 represent a path constructed of the shortest segments connecting each pair of points.

Reverting to FIG. 13, at step 211 edges of the tree graph produced in step 209 are removed from the sorted list that was created in step 205. At this step multiple gaps in multiple isolations of signals may be reported.

After performing step 211 a gap through the ablated sites may optionally be identified based on a new source. When this option is omitted, as indicated by a broken line, control proceeds to final step 213, which is described below. Otherwise, the operator at step 215 selects a point, for example, by a mouse click on the display. Other methods may be used by the operator or chosen automatically to select one or more points of sources that he wishes to isolate.

Next, at step 217 the 3-dimensional intercepts of the mouse position are identified as a pair of vectors that define a line segment. This may be understood by the mouse click defining a ray extending from the mouse pointer into the screen. A virtual 3-dimensional box containing all relevant points, intersects with the ray twice. Each point of intersection has 3-dimensional coordinates. All the ablation site points are centered about the center of the line segment connecting the intersections.

Next, at step 219 a rotation operation is conducted such that the x-axis aligns with the direction of the line segment defined by the mouse click in step 217. The points are then projected onto the x=0 plane. Because the points were centered about the mouse position, the coordinate origin is a convenient point of reference for the rotation.

The next steps describe an iteration over the sorted list of edges, in which the shortest segment that complies with a predetermined gap criteria, e.g., a winding number of ±1 is retained. At step 221 for each edge a graph of the edges is created. This graph is the union of the tree graph with an additional edge. Adding an edge to a tree graph in this manner produces a loop. Thus, this graph has only one loop since the tree graph has no loops and has all of its points connected.

Next, at step 223 a sub-graph of all of the graph vertices that are core components of order 2 is selected. This sub-graph is a pure loop and has no weakly connected elements. In graph theory, a k-degenerate graph is an undirected graph in which every subgraph has a vertex of at most degree k: that is, some vertex in the subgraph touches k or fewer of the subgraph's edge. Degeneracy is also known as the k-core number. For the purpose of this disclosure a sub-graph having weakly connected elements has a k-value less than 2.

Next, at decision step 225, it is determined if the loop of the current sub-graph includes, i.e., encompasses the origin. If a 2-dimensional point is within a 2-dimensional polygon, the sum of the interior angles of the polygon sides should be exactly 360°. One way of determining if the loop includes the origin is to sum the differences of the arctangents of the points in each edge of the loop graph, correcting the range appropriately in order to deal with discontinuities. Since at x<0, y=0 the arctangent jumps from +180° to −180°, the angle coverage of each segment should be corrected to the (−180°, +180°) range. If the final sum is ±360°, the loop includes the origin.

If the determination at decision step 225 is negative, then control returns to step 223 to continue the iteration by generating a new subgraph from the next edge (in order of length).

If the determination at decision step 225 is affirmative, then it is concluded that the gap has been found. The gap is reported at final step 213. The length of the gap is the Euler distance between the 3-dimensional vertices on either side of the gap edge. Optionally, by calculating the lengths of the all edges of the loop graph, more gaps, e.g., any number of smaller gaps can be reported. For the convenience of the operator, by selecting a high contrast color scheme and an objective gap size range, the gaps can be colored according to their lengths.

Figure 18:
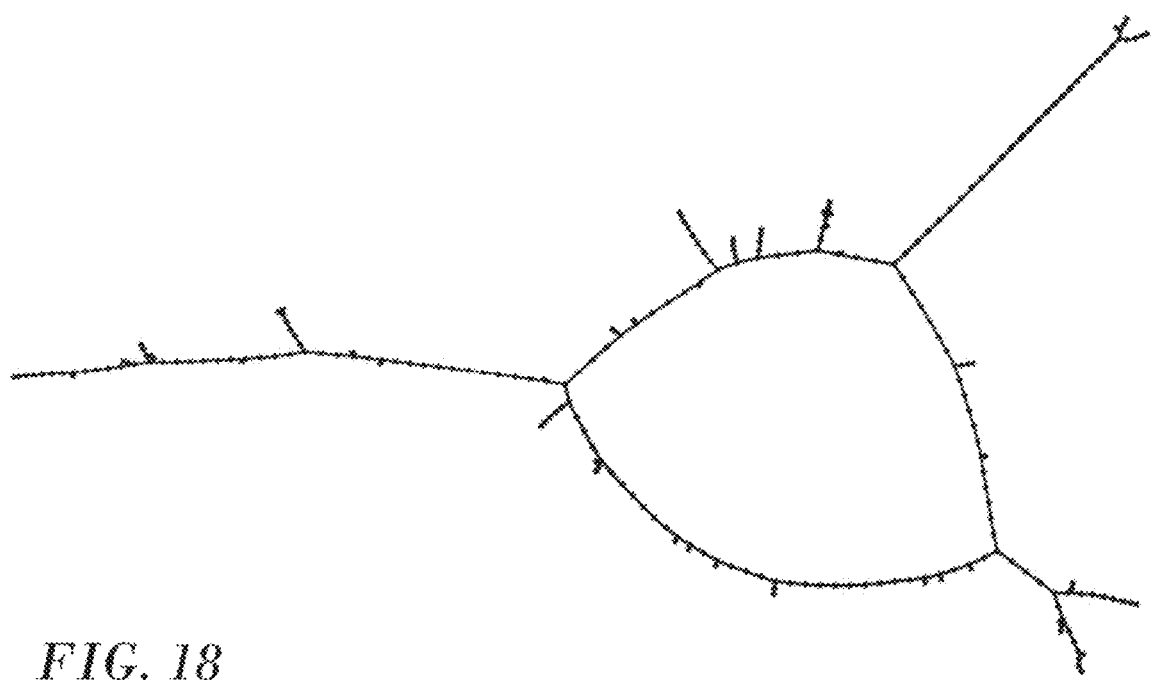
FIG. 18 is an exemplary loop graph that is evaluated in the method shown in FIG. 13, in accordance with an embodiment of the invention.

Reference is now made to FIG. 18, which is an exemplary loop graph in abstract space that is evaluated step 221 in accordance with an embodiment of the invention.

Reference is now made to FIG. 19, which is a composite screen display that was produced in accordance with an embodiment of the invention. A 3-dimensional presentation of ablation points is seen in pane 227. Points projected on a simulation plane are shown in pane 229. A key 231 indicating gap sizes is shown in the upper right portion of the display. A gap 233 measuring 7.5 mm is shown in the pane 227.

Figure 20:
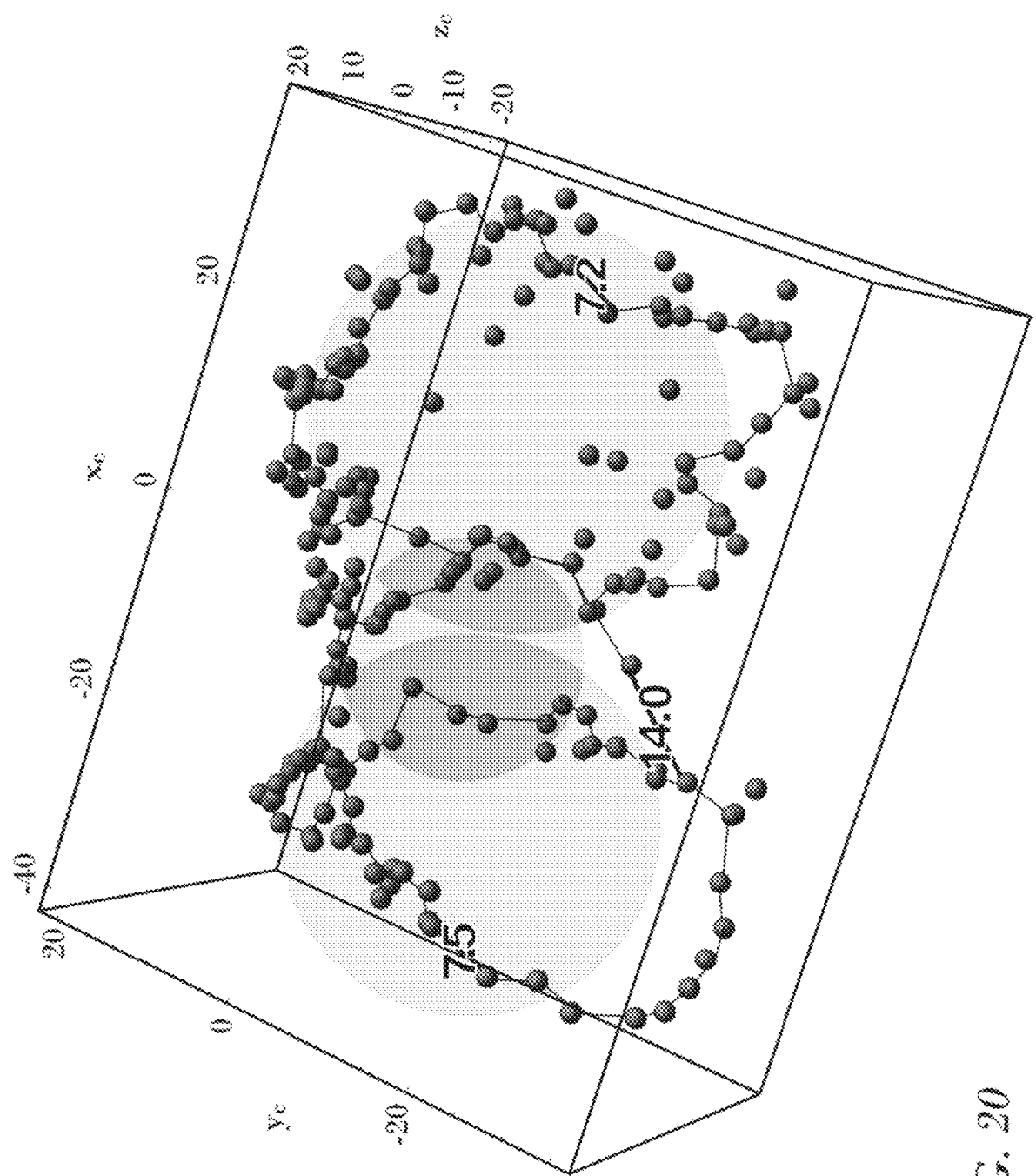
FIG. 20 is a screen display illustrating multiple gaps found in a collection of ablation points in accordance with an embodiment of the invention.

Reference is now made to FIG. 20, which is a screen display illustrating multiple gaps found in a collection of ablation points when the procedure beginning at step 215 is performed and wherein all reasonable sources are found automatically in accordance with an embodiment of the invention. Three gaps were discovered, which are the largest among the gaps discovered by the procedure of FIG. 7 and reported at final step 145. Their sizes are labeled on the figure.

Additional Considerations.

Once the sizes of the lesions of the ablation sites are calculated by a formula, the site radii can be removed from the length of each edge length before sorting. The result will be the largest gap between estimated lesions instead of the largest gap between site centers.

Finding a gap in a line: Once a beginning and end sites are determined, the shortest path can be found using graph theory. The path segments can be sorted and colored objectively as for gap in a loop.

Excluding points: The entire procedure can be performed on a subset of the ablation sites.

Automated gap finding: Given a set of input parameters, the algorithm can search for loops and gaps automatically, as shown in position sensor 21.

Instead of testing if a loop includes the origin in decision step 225 (FIG. 13), the gap criteria for automated gap finding can include:

The minimum number of sites in a loop (e.g. 8).

The minimum size of the loop (e.g. 9 mm, determined by the median distance of the points from the loop center).

The maximum gap opening (e.g. 45°).

The maximum gap size (e.g. 40 mm).

Proposition

The following proof forms a logical basis for the processes described above: Given a set of discrete closed curves on a 2D surface and a point source, the isolation is the curve with unit winding number that is constructed of segments with the smallest segment lengths.

Proof

1. Let us assume that we have generated all of the possible paths from the source to the destination (named the path set).

2. Let us assume further that we have a fine set of segment that construct all possible discrete contours with unit winding number about the source (named the segment set and the contour set, respectively).

3. Each path in the path set intersects with all of the contours in the contour set.

4. Assuming that resistance to current flow is inverse to the size of a contour gap, a path that intersects the contour having the smallest gap experiences the greatest resistance at that gap.

5. Let us collect these segments and name the set the suspected segment set.

6. The least hindered paths are the paths that intersect the segment from the suspected set with the largest segment length. Therefore, this segment has the largest gap in the isolation, and will be part of the isolation.

7. Removing all contours that do not include this segment from the contour set (so that only segments that are part of the remaining contours are left in the segment set and the suspected set), the next largest segment in the suspected set is the next in order cause of current leak, and therefore is also part of the isolation.

8. Repeating this process leaves us with only one contour, which is the one with the segments with the smallest segment length by order, and this contour is the isolation.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method for determining a gap in an ablated region of tissue, comprising the steps of:

ablating a plurality of sites in a heart of a living subject, the sites having respective locations in a 3-dimensional coordinate system;

projecting the locations of the sites onto a simulation plane;

defining a source and a destination; projecting the source and the destination onto the simulation plane, wherein the projected locations of the sites lie between the projected source and the projected destination on the simulation plane;

randomly generating a set of 2-dimensional paths that correspond to 3-dimensional connections between pairs of the projected locations of the sites on the simulation plane extending from the projected source to the projected destination, each path having passages between the projected locations of sites in each pair of projected locations of sites, the passages having respective sizes; and for each of the 2-dimensional paths determining a minimum size of the passages thereof, wherein reporting a gap comprises reporting the largest minimum size of the 2-dimensional paths.

2. The method according to claim 1, wherein the projected locations of the sites lie on an ellipse of best fit, wherein a portion of the projected locations of the sites lie outside the ellipse, further comprising enlarging the ellipse to include all of the projected locations of the sites.

3. The method according to claim 1, further comprising the steps of:

modeling a portion of the heart as a triangular mesh comprising mesh nodes and ablation points, respective ablation points having a nearest mesh node;

from the mesh nodes preparing a grid graph having graph nodes that are connected by undirected edges;

representing the ablation points on the grid graph as corresponding graph nodes of the nearest mesh node thereof; and using the corresponding graph nodes as the projected locations of the sites in the step of generating 2-dimensional paths.

4. A method for determining a gap in an ablated region of tissue, comprising the steps of:

ablating a plurality of sites in a heart of a living subject, the sites having respective locations in a 3-dimensional coordinate system;

building a tree graph from all of the locations of the sites, the tree graph having edges and defining a path constructed of shortest segments between pairs of the sites;

selecting a source, wherein the tree graph has a loop that winds about the source, the loop describing a gap between two of the ablation sites; and reporting a shortest edge in the tree graph that can close the gap as a gap size.

5. The method according to claim 4, further comprising selecting additional sources and iterating the step of building a tree graph using the additional sources.

* * * * *